(12) United States Patent
Meskens et al.

(10) Patent No.: US 8,934,984 B2
(45) Date of Patent: Jan. 13, 2015

(54) BEHIND-THE-EAR (BTE) PROSTHETIC DEVICE WITH ANTENNA

(75) Inventors: Werner Meskens, Opwijk (BE);
Tadeusz Jurkiewicz, Rozelle (AU);
Steve Winnall, Stanmore (AU); Limin Zhong, Denistone (AU)

(73) Assignee: Cochlear Limited, Macquarie University, NSW (AU)

( * ) Notice: Subject to any disclaimer, the term of this patent is extended or adjusted under 35 U.S.C. 154(b) by 1813 days.

(21) Appl. No.: 12/131,867

(22) Filed: Jun. 2, 2008

(65) Prior Publication Data

US 2008/0304686 A1 Dec. 11, 2008

Related U.S. Application Data

(60) Provisional application No. 60/924,800, filed on May 31, 2007, provisional application No. 60/924,807, filed on May 31, 2007.

(51) Int. Cl.
*A61N 1/372* (2006.01)
*A61N 1/08* (2006.01)
*A61N 1/36* (2006.01)

(52) U.S. Cl.
CPC ............... *A61N 1/08* (2013.01); *A61N 1/36032* (2013.01)

USPC .................. 607/55; 607/56; 607/57; 607/135; 607/136; 607/137

(58) Field of Classification Search
USPC ........................ 607/55–57, 136–137
See application file for complete search history.

(56) References Cited

U.S. PATENT DOCUMENTS

| | | | |
|---|---|---|---|
| 4,741,339 A | 5/1988 | Harrison et al. | |
| 6,748,094 B1 | 6/2004 | Tziviskos et al. | |
| 6,766,201 B2 | 7/2004 | Von Arx et al. | |
| 6,924,773 B1 | 8/2005 | Paratte et al. | |
| 7,020,298 B1 | 3/2006 | Tziviskos et al. | |
| 2004/0073275 A1* | 4/2004 | Maltan et al. | 607/57 |
| 2004/0138723 A1* | 7/2004 | Malick et al. | 607/57 |
| 2005/0251225 A1* | 11/2005 | Faltys et al. | 607/57 |
| 2006/0052144 A1* | 3/2006 | Seil et al. | 455/575.1 |

\* cited by examiner

*Primary Examiner* — Christopher D Koharski
*Assistant Examiner* — Natasha Patel
(74) *Attorney, Agent, or Firm* — K&L Gates LLP

(57) ABSTRACT

A BTE prosthetic device for use in a medical system or prosthesis comprises a connector configured to mechanically attach an auxiliary device of the system to the BTE prosthetic device. The connector is electrically connected to a transceiver of the BTE prosthetic device. The connector operates as an electromagnetic antenna for transmitting and/or receiving signals between the BTE prosthetic and other components of the medical system.

27 Claims, 10 Drawing Sheets

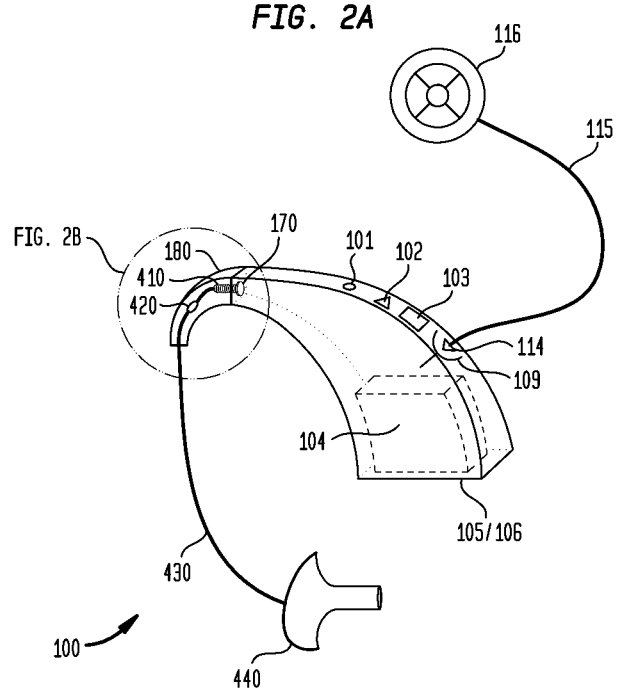
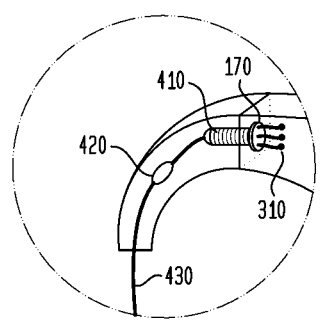

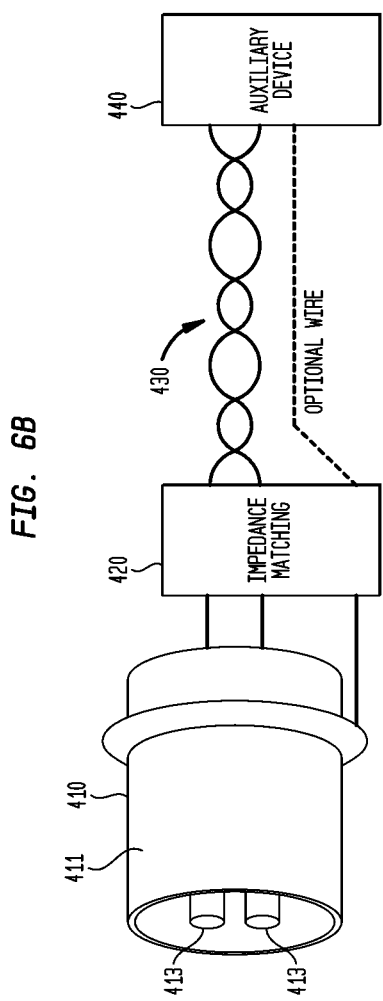

US 8,934,984 B2

BEHIND-THE-EAR (BTE) PROSTHETIC DEVICE WITH ANTENNA

CROSS-REFERENCE TO RELATED APPLICATIONS

This application claims priority to U.S. Provisional Patent Application No. 60/924,800, filed on May 31, 2007, and U.S. Provisional Application No. 60/924,807, filed on May 31, 2007, both of which are hereby incorporated by reference herein.

BACKGROUND

1. Field of the Invention

The present invention relates generally to hearing prostheses and, more particularly, to a behind-the-ear (BTE) prosthetic device with an antenna.

2. Related Art

Hearing aid prostheses, such as those designed to be worn behind the ear of the recipient, commonly referred to as behind-the-ear (BTE) devices, may be components of conventional hearing aids, cochlear implants, and/or the like. BTE devices, whether implemented as a component of a hearing aid, cochlear implant, middle ear implant or other hearing prosthesis, are collectively and generally referred to herein as a BTE prosthetic devices.

Conventional hearing aids may include external sound processors which input the processed (and amplified) sound in the ear by an external, or in-the ear speaker. Cochlear implants have been developed to assist people who are profoundly deaf or severely hearing impaired, by enabling them to experience a hearing sensation representative of the natural hearing sensation. In most such cases, these individuals have an absence of or destruction of the hair cells in the cochlea which naturally transduce acoustic signals into nerve impulses which are interpreted by the brain as sound. The cochlear implant therefore bypasses the hair cells to directly deliver electrical stimulation to the auditory nerves with this electrical stimulation being representative of the sound.

Cochlear implants have traditionally comprised two parts, an external component and an implanted receiver/stimulator unit. The external component may be been worn on the body of a recipient, classically as a BTE prosthetic device. The purpose of such a BTE prosthetic device has been to detect external sound using a microphone and convert the detected sound into a coded signal through an appropriate speech processing strategy.

This coded signal is then sent via a transcutaneous link to receiver/stimulator unit which is implanted in the mastoid bone of the recipient. A transcutaneous link is a magnetic induction link between a coil antenna of the implant and an externally applied coil antenna. The receiver/stimulator unit processes the coded signal into a series of stimulation sequences which are then applied directly to the auditory nerve via a series of electrodes positioned within the cochlea proximal to the modiolus of the cochlea.

The externally applied coil antenna typically forms part of a headpiece, which is applied in close proximity of the coil antenna of the implant and is connected to an external speech processor, such as a device for behind the ear. The magnetic induction link (established in a reactive near-field) typically allows bidirectional communication and power transfer towards the implant.

SUMMARY

In accordance with aspects of the present invention, a behind-the-ear (BTE) prosthetic device for use in a medical system is provided. The BTE prosthetic device comprises: a connector configured to mechanically attach an auxiliary device to the BTE prosthetic device; and a transceiver comprising one or more of an RF transmitter and an RF receiver, wherein the connector is electrically connected to the RF transceiver, and wherein the connector operates as an electromagnetic antenna for wireless communication between the BTE prosthetic device and one or more other components of the system.

In accordance with other aspects of the present invention, a cochlear implant system is provided. The cochlear implant system comprises: an implantable component; an external auxiliary component; and a behind-the-ear (BTE) prosthetic device comprising: a connector configured to mechanically attach said auxiliary device to said BTE prosthetic device; and an transceiver comprising one or more of an RF transmitter and an RF receiver, wherein said connector is electrically connected to said transceiver, and wherein said connector is configured to operate as an electromagnetic antenna for wireless communication between said BTE prosthetic device and said implantable component.

BRIEF DESCRIPTION OF DRAWINGS

Illustrative embodiments of the present invention are described herein with reference to the accompanying drawings, in which:

FIG. 2A illustrates a BTE prosthetic device having an ear hook and auxiliary device with extension antenna in accordance with embodiments of the present invention;

FIG. 2B illustrates a close-up view of a portion of the BTE prosthetic device of FIG. 2;

FIG. 6B illustrates a twin-axial connector in accordance with one embodiment of the present invention;

DETAILED DESCRIPTION

Aspects of the present invention are generally directed to a connector for a prosthesis configured to be worn behind the ear of an individual or recipient, commonly referred to as behind-the-ear (BTE) devices. BTE devices may be a component of a conventional hearing aid and/or cochlear implant, or a component of any other medical systems or prosthesis. BTE devices, whether implemented as a component of a hearing aid, cochlear implant, middle ear implant or other medical systems/prosthesis, are collectively and generally referred to herein as a BTE prosthetic devices.

In certain aspects of the present invention, a BTE prosthetic device for use in a medical system or prosthesis, (collectively and generally referred to as medical system herein) comprises a connector configured to mechanically attach an auxiliary device of the system to the BTE prosthetic device. The connector is electrically connected to a transceiver of the BTE prosthetic device. The transceiver may comprise any combination of a transmitter and/or an receiver. Furthermore, the transceiver may comprise only a transmitter or a receiver. The connector is configured to operate as an electromagnetic antenna for transmitting and/or receiving signals between the BTE prosthetic and other components of the medical system. The electromagnetic antenna may be, for example, operable in the far-field.

Figure 1:
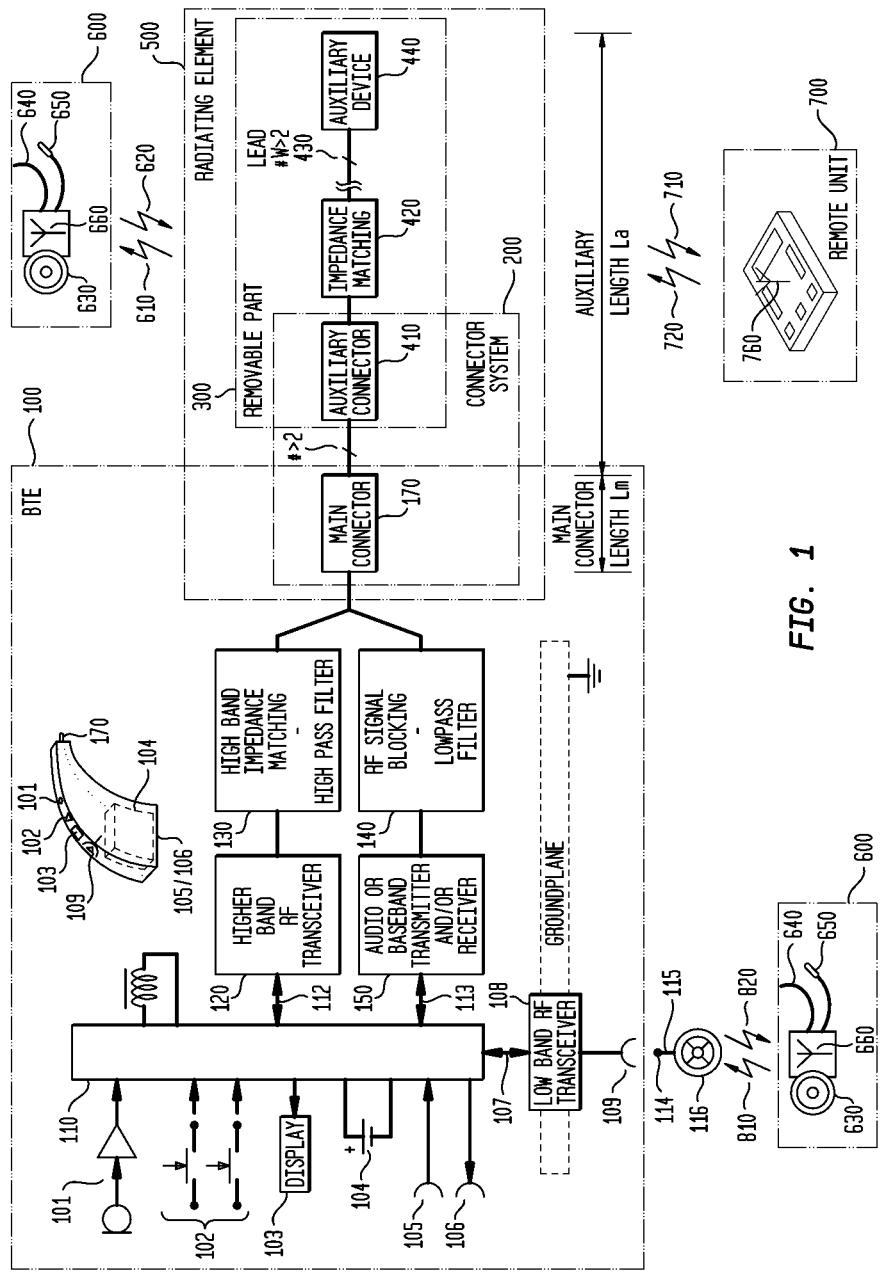
FIG. 1 is a schematic block diagram of a behind-the-ear (BTE) prosthetic device having an integrated antenna and connector in accordance with embodiments of the present invention.

As noted, embodiments of the present invention may be implemented with a number of BTE prosthetic devices in a variety of medical systems. Embodiments of the present invention will be described herein with reference to one specific type of BTE prosthetic device and medical system, namely a BTE prosthetic device which is a component of a partially implantable hearing aid system. FIG. 1 illustrates such a partially implantable hearing aid system, comprising BTE prosthetic device 100 in communication with one or more cochlear stimulating implants, shown generally as implants 600 and one or more remote units 700. Implants 600 may each comprise a variety of implantable cochlear stimulating devices, such as an implantable electrode arrays, middle ear implants, or the like. As described in more detail below, BTE prosthetic device 100 may communicate with other components of the partially implantable hearing aid system via one or more wireless communication links, shown as communication links 610, 620, 710, 720, 810 and 820.

In the illustrated embodiment of FIG. 1, BTE prosthetic device 100 comprises a microphone 101 to receive acoustic sounds, and a signal processor 110. BTE prosthetic device 100 converts and processes the received acoustic sounds received by microphone 101, or various other received auditory signals, to a format which may used by the implants 600. In accordance with the illustrated embodiments, BTE prosthetic device 100 further comprises one or more transceivers 108 which may transmit processed signals to implants 600.

BTE prosthetic device 100 has sufficient persistent and non-persistent memory. Furthermore, BTE prosthetic device 100 is powered by a battery 104. Additional controls 102 and interfaces 103 facilitate human interaction with the hearing aid system. In certain embodiments, the main housing of BTE prosthetic device 100 may accept removable plug-in modules, such as batteries, an ear hook, a headpiece, etc. BTE prosthetic device 100 may also be provided with input and output jacks 105 and 106.

As noted, a variety of cochlear stimulating implants may be used in accordance with embodiments of the present invention. FIG. 1 illustrates specific implants 600 which comprise an implantable electrode array 640 that stimulate the recipient's cochlea with electrical signals. The implant converts the signals received from the BTE prosthetic device 100 into stimuli signals and then applies them to the cochlea via electrode array 640. Depending on cause of the recipient's deafness, implant 600 may optionally comprise a mechanical implantable actuator 650 configured to stimulate middle or inner ear parts, in addition to, or in place of, electrode array 640.

In embodiments of the present invention, BTE prosthetic device 100 comprises a lower radio frequency (RF) band transceiver 108 for wireless communication over a magnetic induction link, such as links 810 and 820. Transceiver 108 may be configured to transmit and/or receive wireless communications. Low RF band transceiver 108 may be connected, in certain embodiments, to a connector socket 109, which accepts a plug 114 of a headpiece 116. Headpiece 116 comprises an extension cable 115 between plug 114 and an antenna coil or closed-wire loop 116. Antenna coil 116 is configured to transmit signals to coil antenna 630 of an implant 600, and/or receive signals from coil antenna 630. Antennas 116 and 630 may be placed in close proximity of each other.

The above-described communication link 810 and 820 between BTE prosthetic device 100 and implant 600 operates in the reactive near-field, by magnetic induction in a non-propagating quasi-static magnetic field. Both bidirectional data transfer and power transfer towards the implant are possible.

In accordance with certain embodiments of the present invention, communication between components of a medical system may occur in a near-field or far EM-field, via, for example, electromagnetic field propagation. This type of communication has the advantage that it takes place over larger distances, which would permit components of the communication link to be spaced apart by larger distances than permitted in a conventional RF link. Furthermore, wireless communication between the BTE prosthetic device 100 and other external devices 700 may also preferably take place in the propagating far-field. An antenna tuned to the frequency range of operation is generally used for efficient communication using the EM-field. Whereas a magnetic induction link uses a coil or closed-wire antenna, transmission and reception by electromagnetic field propagation may be carried out with open-ended antennas.

According to aspects of the present invention, an electromagnetic antenna is integrated with a mechanical connector which is used in BTE prosthetic device 100 to mechanically attach various components or other devices to the BTE prosthetic device. According to one embodiment of the invention, and referring to FIGS. 1 and 2, an electromagnetic antenna can be incorporated into a connector, shown as connector 170. In the specific illustrated embodiment of FIGS. 1 and 2, connector 170 of the BTE prosthetic device 100 is configured to mechanically attach an ear hook 180 to BTE prosthetic device 100. Connector 170 may also be configured to operate as, or function as, as an electromagnetic antenna for transmission of, or reception of signals between BTE prosthetic device 100 and one or more other components of the implantable hearing system.

Ear hook 180 provides a mounting means for holding BTE prosthetic device 100 behind the ear of the recipient. Connector 170 may include, for example, threaded attachment elements, a snap-lock or click-fit mechanism or any other removable mechanical fastening means now know or later developed for attaching connector 170 to BTE prosthetic device 100. In certain embodiments, one or more conducting wires 310 provide an electrical coupling between connector 170 and components of BTE prosthetic device 100, such as the printed circuit board of the BTE prosthetic device.

As noted, connector 170 may also be configured for electrical connection with an auxiliary device. For example, connector 170 may be provided with, or comprise, for example, a socket accepting a plug 410 of an auxiliary device 440, such as an earphone.

Figure 3A:
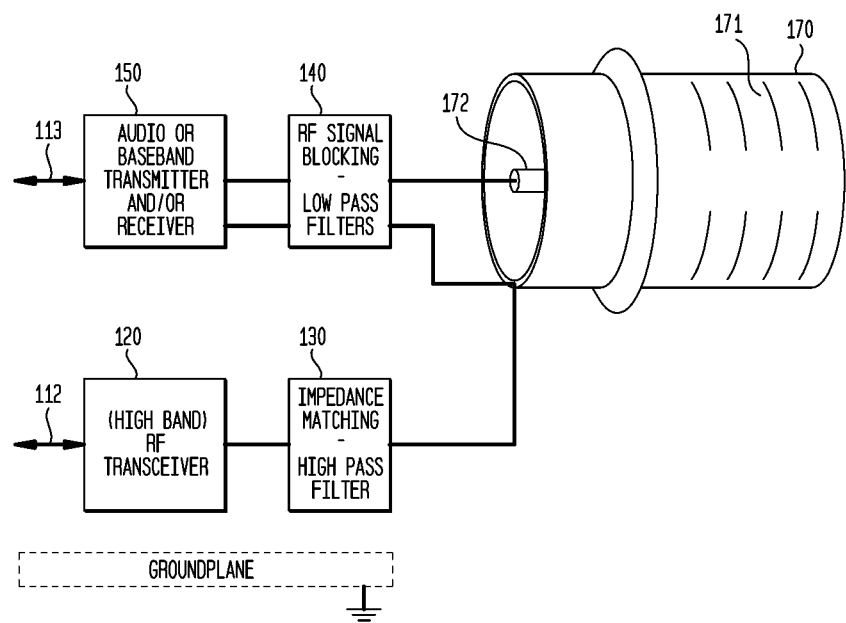
FIG. 3A illustrates a co-axial male connector in accordance with one embodiment of the present invention.
Figure 3B:
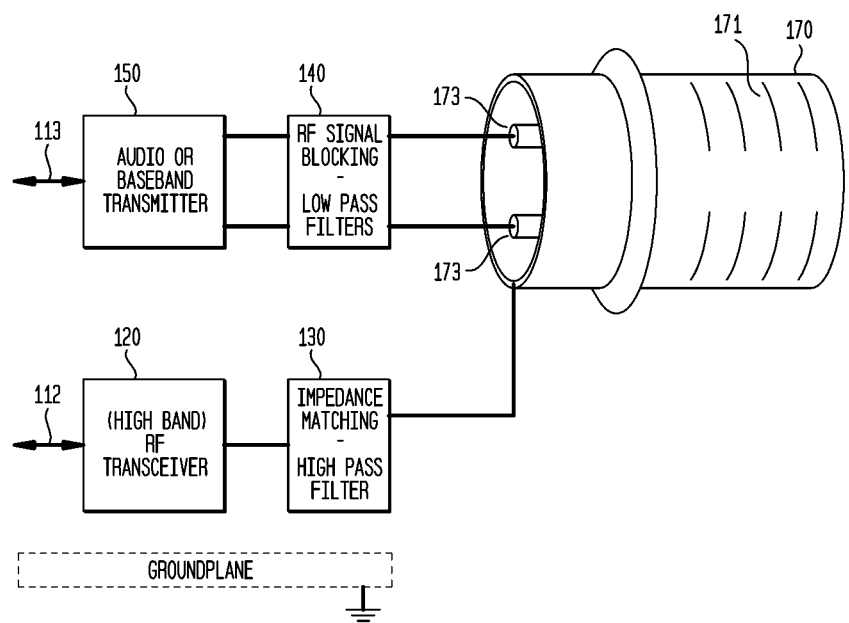
FIG. 3B illustrates a twin-axial male connector in accordance with one embodiment of the present invention.

Some possible embodiments of connector 170 are illustrated in FIG. 3. FIG. 3A illustrates connector 170 as a coaxial electrical and mechanical connector type. FIG. 3B illustrates connector 170 as a twin-axial electrical and mechanical connector type. In certain embodiments, connector 170 may comprise an outer body 171 which is cylindrical and may be made of an electrical conducting material.

In the embodiments of FIG. 3A, coaxial connector 170 comprises one electrically conductive receptacle 172, in addition to the conductive outer body 171. Hence, the outer body 171 and the receptacle 172, which are electrically shielded from each other, constitute an input or output jack for transmitting and/or receiving electrical signals, such as audio signals, to and from the attached auxiliary device 440. Therefore, BTE prosthetic device 100 may comprise an audio or baseband transmitter and/or receiver (transceiver) 150, linked at 113 to signal processor 110. Audio/baseband transceiver 150 is connected to the outer body 171 and to the receptacle 172 of connector 170.

The outer body 171 is configured to operate as, or function as, as part of an electromagnetic antenna for transmitting or receiving signals. As noted, connector 170 may be used by BTE prosthetic device 100 to transmit, or receive signals from, one or more other components of the implantable hearing system. In certain embodiments, outer body 171 operates as an open-ended wire, a monopole, stub, helix or helical wound coil, meander or dipole electromagnetic antenna. The electromagnetic antenna is operable in a variety of frequency ranges, including above 100 KHz, and in some embodiments in a frequency range above 30 MHz or 3 GHZ. As such, in the illustrated embodiments, connector 170 is configured for electrical connection of an auxiliary device to BTE prosthetic device 100 and for transmission and/or reception of signals between components of the hearing aid system.

BTE prosthetic device 100 may comprise an RF high band transceiver 120, linked via link 112 to signal processor 110. RF transceiver 120 is connected to the outer body 171. In order to improve the reception or transmission of power efficiency of outer body 171 as an antenna, an impedance matching circuit 130 may be provided between transceiver 120 and outer body 171. A high-pass or band-pass filter 130 and a low-pass or band-pass filter 140 ensure a separation of the radiated RF signals and the signals transferred over the jack combination 171/172. Hence, filter 140 blocks high RF band signals and prevents them from propagating to the transceiver 150 and high-pass filter 130 blocks low band signals (e.g. audio, baseband) and prevents them from leaking into transceiver 120.

Connector 170 may comprise multiple separate electrical conduction paths for conductive transmission of electrical signals. Likewise, outer body 171 of connector 170 may or may not transfer electrical signals. In certain embodiments, connector 170 protrudes from BTE prosthetic device 100.

FIG. 3B illustrates an additional embodiment of the present invention. As shown, the twin-axial connector 170 of FIG. 3B comprises two electrically conductive receptacles 173, in addition to a conductive outer body 171. Hence, the receptacles 173, which are electrically shielded from each other, constitute a jack for transmitting and/or receiving electrical signals, such as audio signals, to and from an auxiliary device 440 attached thereto. Therefore, BTE prosthetic device 100 may comprise an audio or baseband transmitter and/or receiver (transceiver) 150, linked at link 113 to signal processor 110. Audio/baseband transceiver 150 is connected to the receptacles 173.

In the embodiments of FIG. 3B, the outer body 171 may operate as an electromagnetic antenna similar to that described above with reference to FIG. 3A. Therefore, BTE prosthetic device 100 may comprise a high RF band transceiver 120, linked at link 112 to signal processor 110. RF transceiver 120 is connected to the outer body 171. In certain embodiments, to improve receive or transmit power efficiency of the antenna, an impedance matching circuit 130 is provided between transceiver 120 and the antenna (outer body) 171 for making the impedance of the antenna, as seen by the transceiver, real. A high-pass or band-pass filter 130 and a low-pass or band-pass filter 140 may ensure a separation of the radiated RF signals and the signals transferred over the jack 173. The low-pass and high-pass filters may be optional in the case of FIG. 3B, as the two types of signals (to/from transceivers 150 and 120) may not share the same electrical paths as in the case of FIG. 3A. However, radiated RF signals may be captured by the receptacles 173 and may interfere with the operation of the baseband transceiver 150. Likewise, the antenna 171 may capture low band signals. Hence, filter 140 blocks high RF band signals and prevents them from propagating to the transceiver 150 and high-pass filter 130 blocks low band signals and prevents them from leaking to transceiver 120.

A low band signal preferably comprises frequencies below or equal to about 100 KHz, while high RF band signals comprise signals situated in the radio spectrum above 100 KHz, such as, for example, 2.4 GHz. For the purposes of the present invention, high RF band signals are signals in the VHF (very high frequency), UHF (ultra high frequency), or higher frequency range. The low-pass filter 140 and the high-pass filter 130 may function as a band diplexer. The antenna 170 may be arranged to transmit or receive data such as telemetry, control data, signalling data and audio streaming.

Figure 4:
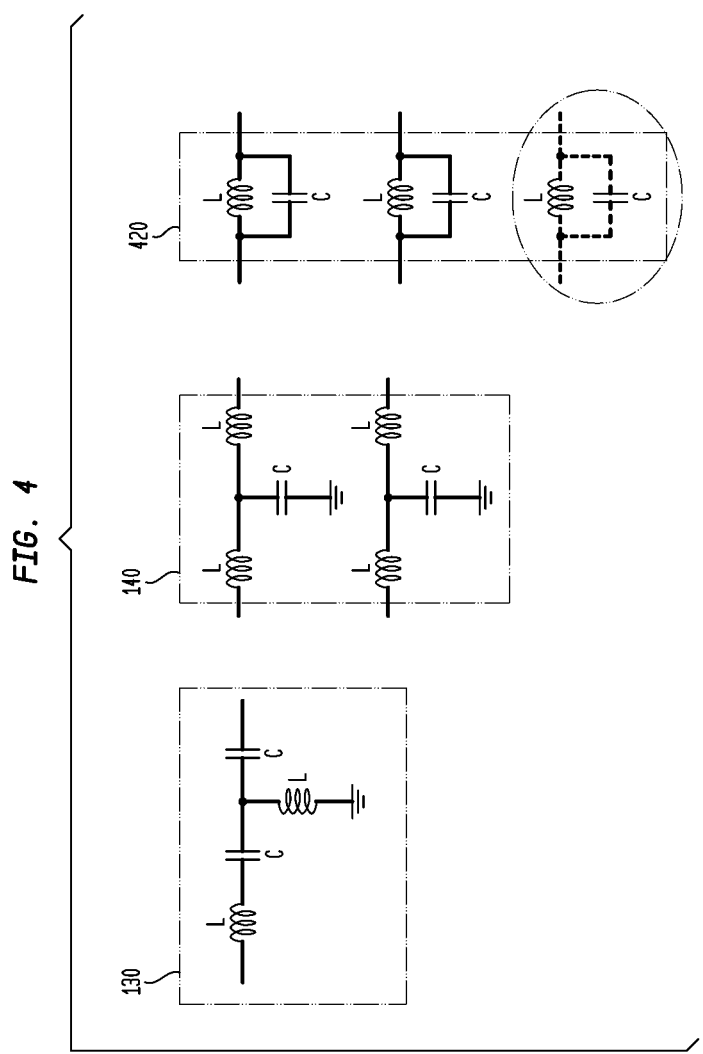
FIG. 4 illustrates embodiments of antenna impedance matching units and low-pass and high-pass filters in accordance with embodiments of the present invention.

FIG. 4 illustrates a possible implementation of the impedance matching circuit and high-pass filter 130 and the low-pass filter 140 in accordance with embodiments of the present invention. As shown in FIG. 4, such filters may comprise, for example, lumped resistors, capacitors and inductors, or other elements now know or later developed, the values of which may be chosen in function of the operating frequencies of the devices. The audio or baseband signals applied to or received from the auxiliary device are much lower in frequency than the RF signals radiated by the antenna. A third-order filtering may be sufficient in most cases.

Antenna impedance matching circuit 130 may be used to alter the effective electrical length of an antenna by matching it with additional capacitance or inductance. Antenna impedance matching circuit 130 tunes the radiating system of the antenna at the operational radio frequency, in order to obtain resonance. In one such case, the RF transceiver 120 sees the antenna as a purely resistive load. Such a matching circuit is optional.

Figure 5:
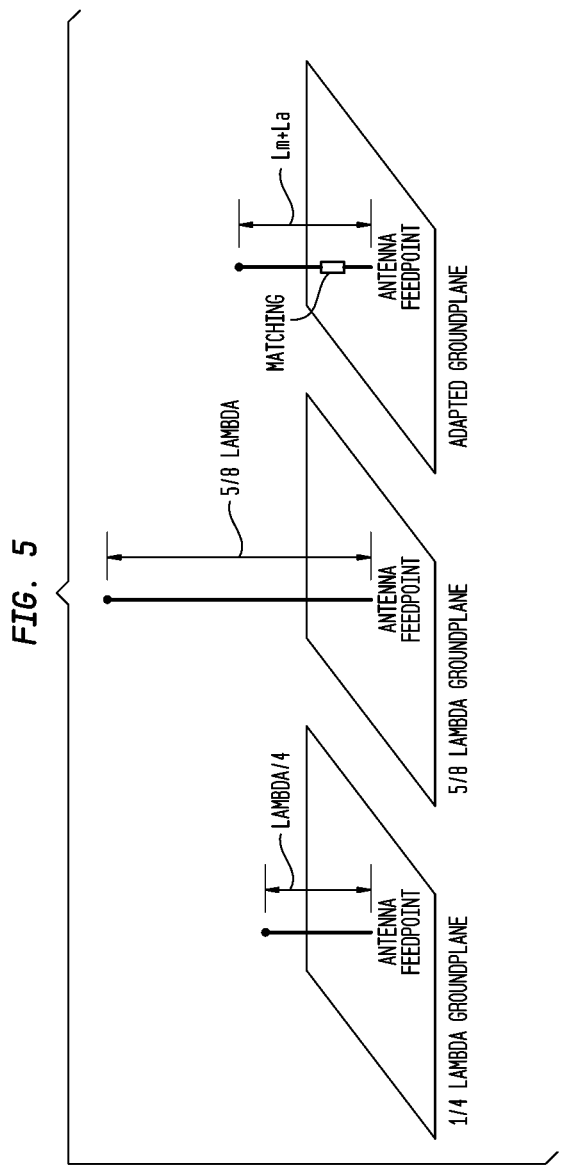
FIG. 5 schematically illustrates different matched ground-plane antennas.

As noted, antenna 171 may operate as an open-ended wire antenna, such as a monopole, a dipole, a groundplane, a helix, a helical wound, or a meander antenna. FIG. 5 shows a simplified representation of a quarter $\lambda$, a $\frac{5}{8}\lambda$ and a matched groundplane antenna. The physical construction of antenna 171 of the present invention can be considered as a groundplane antenna, with the housing of BTE prosthetic device or its printed circuit board as ground plane element and the connector 170 as radiating or receiving element. From an antenna-matching viewpoint, it is preferable to choose the total physical length of the antenna (e.g. the length of the outer body 171 of connector 170) to $\lambda/4$ or $\frac{5}{8}\lambda$, with $\lambda$ the wavelength of the operating frequency of the antenna.

When the wavelength is very small, e.g. at 2.4 GHz, antenna matching is performed on the connector 170. At lower frequencies, an antenna with increased physical length is used. This may be achieved by incorporating, for example, into the auxiliary device which is attached to the BTE prosthetic device, an extension of antenna 170. Such an arrangement is illustrated in FIG. 1 with device 300.

In the illustrated embodiments, device 300 comprises all elements necessary for operation as an electromagnetic antenna, such as a ground plane and radiating/receiving elements. As such, device 300 is referred to as an auxiliary antenna device. The auxiliary antenna device 300 may be removably attached to the BTE prosthetic device 100 and comprises a connector plug 410 for acceptance by connector 170, the auxiliary device 440, a lead 430 between connector and auxiliary device and an optional antenna impedance matching circuit 420. The lead 430 is a naturally preferred object for use as radiating/receiving element and lends itself as an extension of antenna 170.

When auxiliary antenna device 300 is coupled to connector antenna 170, an antenna 500 is obtained with increased length over the antenna provided by connector antenna 170 alone. The total physical length of antenna 500 is the sum of the length Lm of the connector 170 (base antenna) and the length La of auxiliary antenna 300. The auxiliary antenna device 300 may comprise a matching circuit 420 in additional to the matching circuit 130 of connector 170.

The integration of a removable auxiliary antenna allows to improve radiating efficiency due to a physical extension of the radiating element. The auxiliary antenna devices 300 may allow antennas matched for different operating frequencies. The auxiliary antenna devices 300 may additionally allow antennas of different physical lengths for a same operating frequency. In the latter case, because of the different physical lengths, different impedance matching circuits should be implemented. Such embodiments, allow BTE prosthetic device 100 to be very versatile in the field of wireless communication and communicate with different devices over different RF bands.

Figure 6A:
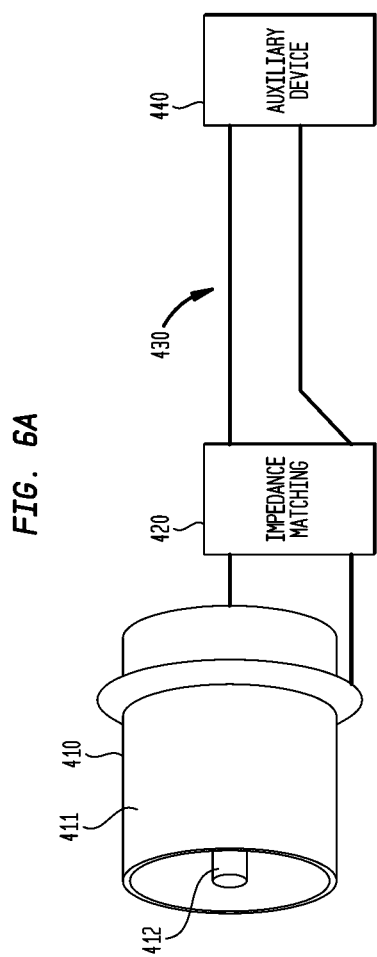
FIG. 6A illustrates a co-axial connector in accordance with one embodiment of the present invention.

FIGS. 6A and 6B generally illustrates the components of auxiliary antenna device 300 in accordance with certain embodiments. Coaxial connector plug 410 of FIG. 6A is arranged for fitting into coaxial connector socket 170 of FIG. 3A. The twin-axial connector plug 410 is configured to fit into twin-axial connector socket 170 of FIG. 3B. A lead 430 comprising two or more conductive wires links connector plug 410 and impedance matching circuit 420, such as any of those shown in FIG. 4, to the auxiliary device 440. Lead 430 may conduct low-band electrical signals (e.g. audio signals) from BTE prosthetic device 100 to the auxiliary device 440 or vice versa.

In the case of a coaxial connector system 200, comprising socket 170 and plug 410 (FIGS. 3a and 6a), electrical connection with BTE prosthetic device 100 is obtained by electrical contact between receptacle 172 and plug 412, and between the outer bodies 171 and 411 of the connectors. In the case of a twin-axial connector system 200, comprising socket 170 and plug 410 (FIGS. 3b and 6b), the electrical connection with the BTE prosthetic device is obtained by electrical contact between the two receptacles 173 and plugs 413, and optionally additionally between the outer bodies 171 and 411 of the connectors.

Returning to FIG. 1, antenna 170, or the extended antenna 500, allows wireless communication in a radio frequency band between a BTE prosthetic device 100 and remote devices. Such devices may be a remote control unit 700, provided with an antenna 760 for wireless communication in the same frequency band. A bidirectional wireless communication link 710, 720 may be established between BTE prosthetic device 100 and remote control unit 700. The BTE prosthetic device 100 may also communicate wirelessly with cochlear implant 600, both through a magnetic induction link 810, 820 by aid of headpiece 116, and through a radio frequency electromagnetic link 610, 620 by the use of antennas 500 or 170 of the BTE prosthetic device and RF antenna 660 of the cochlear implant.

Figure 7:
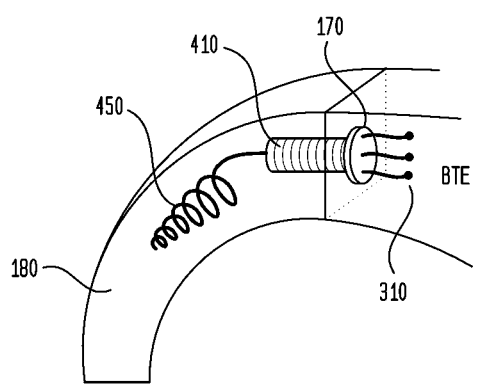
FIG. 7 illustrates a BTE prosthetic device having an ear hook mechanically attached thereto via a connector in accordance with embodiments of the present invention.

FIG. 7 illustrates an additional embodiment for an auxiliary antenna device 450 for use as extension of antenna 170. Antenna 450 is constituted by a helically wound antenna, and is incorporated into ear hook 180.

In accordance with certain embodiments, an auxiliary device may comprise an external plug-in device, such as an in-the-ear speaker. According to other aspects of the present invention, an antenna device comprises a second connector for fitting into the connector of BTE prosthetic device 100, an impedance matching circuit and a lead. The impedance matching circuit is tuned to the impedance of the lead, whereby the lead is operable as an extension of the electromagnetic antenna. The second connector is the counterpart of the connector of the hearing aid device. The second connector may be a plug or a socket.

Figure 8:
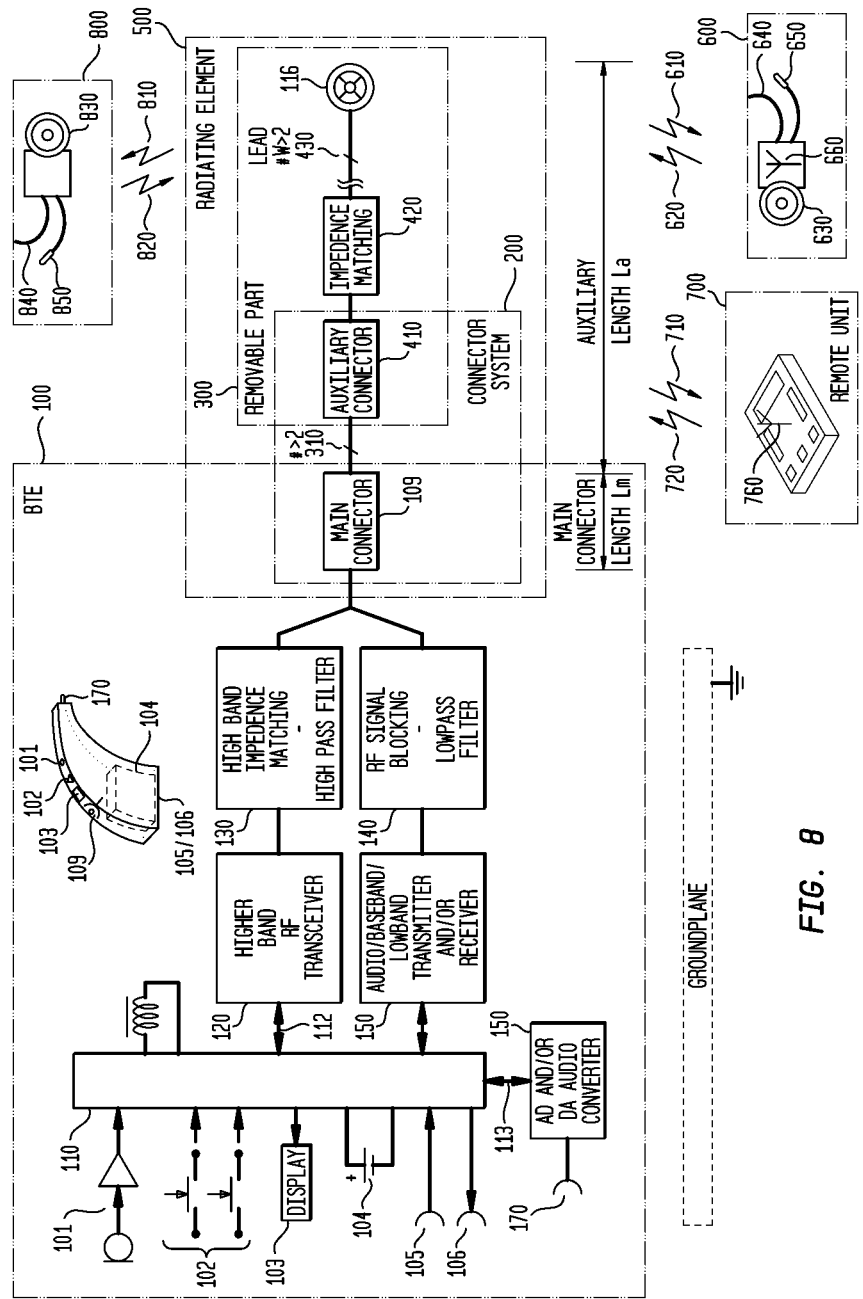
FIG. 8 is a block diagram of a BTE prosthetic device in accordance with embodiments of the present invention.

The antenna in accordance with embodiments of the present invention is not only restricted to connector 170 of an ear hook. FIG. 8 shows an alternative embodiment of the present invention wherein the antenna is incorporated into connector socket 109 of headpiece 116. In such embodiments, connector socket 109 may be implemented in a substantially similar manner as that described above with reference to connector socket 170. In the specific embodiments in which headpiece 116 is additionally used as an auxiliary RF antenna device, the removable device 300 may comprise an auxiliary connector 410 arranged for being accepted by connector 109, an impedance matching unit 420 and a headpiece 116, connected to the auxiliary connector 410 by a lead comprising two or more wires.

As discussed above with reference to FIG. 1, the BTE prosthetic device 100 may communicate wirelessly with an implant 600, which is provided with both a magnetic induction coil antenna 630 and an RF EM-field antenna 660. Coil antenna 630 may communicate with headpiece 116 when closely coupled. Communication over RF antennas 500 and 660 may be established simultaneously, or consecutively in time with the communication over antennas 116 and 630.

In the case that a implant, such as implant 800, is not provided with an RF antenna, wireless communication between BTE prosthetic device 100 and cochlear implant 800 may be established over a magnetic induction link 810, 820 using coil antennas 116 and 830, e.g. for transmitting stimuli signals to an electrode array 840 and/or actuator 850. Simultaneously, the BTE prosthetic device may communicate over antenna 500 with other devices, such as remote control unit 700.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. For example, as one of ordinary skill in the art would appreciate, the present invention provides improved or at least alternative wireless communication possibilities compared to prior art devices and wireless communication methods. Active implantable medical devices envisaged by the present invention include, but are not limited to, cochlear implants, nerve stimulators, pace makers, glucose meters, and any other type of active implantable medical device requiring wireless communication.

U.S. Provisional Patent Application No. 60/924,800, filed on May 31, 2007, and U.S. Provisional Application No. 60/924,807, filed on May 31, 2007, are hereby incorporated by reference in their entirely herein. Similarly, all other patents and publications discussed herein are incorporated in their entirety by reference thereto.

The invention claimed is:

1. A behind-the-ear (BTE) prosthetic device for use in a medical system comprising:
   a connector configured to mechanically attach an ear hook to said BTE prosthetic device; and
   a transceiver comprising one or more of an RF transmitter and an RF receiver,
   wherein said connector is electrically connected to said transceiver, and wherein said connector is configured to operate as an electromagnetic antenna for wireless communication between said BTE prosthetic device and one or more other components of said system;
   wherein said connector comprises an electrically conductive outer body configured to be connected to said transceiver.

2. The BTE prosthetic device of claim 1, wherein said connector is configured to operate as an electromagnetic antenna in the electromagnetic wave propagation field.

3. The BTE prosthetic device of claim 1, wherein said connector is configured to operate as an open-ended wire antenna.

4. The BTE prosthetic device of claim 3, wherein said connector operates as an open-ended wire antenna selected from a group comprising monopole, stub, helix or helical wound coil, meander and dipole antennas.

5. The BTE prosthetic device of claim 1, further comprising an antenna impedance matching unit connected to said connector.

6. The BTE prosthetic device of claim 1, wherein said connector is further configured to electrically connect said ear hook to said BTE prosthetic device, and wherein said connector comprises a plurality of separate electrical conduction paths for transmission of electrical signals.

7. The BTE prosthetic device of claim 1, wherein said connector protrudes from said BTE prosthetic device.

8. The BTE prosthetic device of claim 1, wherein said connector is configured to mechanically attach said ear hook to said BTE prosthetic device by way of at least one of a threaded attachment mechanism, a snap-lock mechanism and a click-fit mechanism.

9. The BTE prosthetic device of claim 1, wherein said system comprises first and second coil antennas separate from said electromagnetic antenna, and wherein said connector is configured to mechanically attach said first coil antenna to said BTE prosthetic device, said first coil constructed and arranged for magnetic inductive coupling with said second coil antenna.

10. The BTE prosthetic device of claim 1, wherein said system further comprises an antenna device configured to be attached to said connector of said BTE prosthetic device, said antenna device comprising:
    a second connector configured to be attached to said connector of said BTE prosthetic device;
    an impedance matching circuit; and
    a lead configured to be attached to said second connector, wherein the impedance matching circuit adapts the impedance of said lead to the impedance of said transceiver of said BTE prosthetic device, and wherein said lead is operable as an extension of said electromagnetic antenna.

11. The BTE prosthetic device of claim 10, wherein said connector of said BTE prosthetic device, said second connector of said antenna device and said lead are collectively operable as an electromagnetic antenna.

12. The BTE prosthetic device of claim 1, further comprising:
    a housing containing at least one electronic component of the BTE prosthetic device, wherein the housing is contoured to fit behind an ear, wherein
    the connector protrudes directly from the housing.

13. The BTE prosthetic device of claim 1, further comprising:
    a housing containing at least one electronic component of the BTE prosthetic device, wherein the housing extends in a generally arcuate manner from a first end to a second end of the housing, wherein
    the connector protrudes from the housing no further than a first distance, and
    a distance of arcuate extension of the housing from the first end to the second end is substantially more than the first distance.

14. A cochlear implant system, comprising:
    an implantable component;
    an ear hook; and
    a behind-the-ear (BTE) prosthetic device comprising:
        a connector configured to mechanically attach said ear hook to said BTE prosthetic device; and
        a transceiver comprising one or more of an RF transmitter and an RF receiver, wherein said connector is electrically connected to said transceiver, and wherein said connector is configured to operate as an electromagnetic antenna for wireless communication between said BTE prosthetic device and said implantable component;
        wherein said connector comprises an electrically conductive outer body configured to be connected to said transceiver.

15. The cochlear implant of claim 14, wherein said connector is configured to operate as an electromagnetic antenna in the electromagnetic wave propagation field.

16. The cochlear implant of claim 14 wherein said connector is configured to operate as an open-ended wire antenna.

17. The cochlear implant of claim 16, wherein said connector operates as an open-ended wire antenna selected from a group comprising monopole, stub, helix or helical wound coil, meander and dipole antennas.

18. The cochlear implant of claim 14, wherein said BTE prosthetic device further comprises an antenna impedance matching unit connected to said connector.

19. The BTE prosthetic device of claim 14, further comprising:
    a housing containing at least one electronic component of the BTE prosthetic device, wherein the housing is contoured to fit behind an ear, wherein
    the connector protrudes directly from the housing.

20. The BTE prosthetic device of claim 14, further comprising:
    a housing containing at least one electronic component of the BTE prosthetic device, wherein the housing extends in a generally arcuate manner from a first end to a second end of the housing, wherein
    the connector protrudes from the housing no further than a first distance, and
    a distance of arcuate extension of the housing from the first end to the second end is substantially more than the first distance.

21. The cochlear implant of claim 14, wherein said connector is further configured to electrically connect said ear hook to said BTE prosthetic device, and wherein said connector comprises a plurality of separate electrical conduction paths for transmission of electrical signals.

22. The cochlear implant of claim 14, wherein said connector protrudes from said BTE prosthetic device.

23. The cochlear implant of claim 14, wherein said connector is configured to mechanically attach said ear hook to said BTE prosthetic device by way of at least one of a threaded attachment mechanism, a snap-lock mechanism and a click-fit mechanism.

24. The cochlear implant of claim 14, further comprises first and second coil antennas separate from said electromagnetic antenna, and wherein said connector is configured to mechanically attach said first coil antenna to said BTE prosthetic device, said first coil constructed and arranged for magnetic inductive coupling with said second coil antenna.

25. The cochlear implant of claim 14, further comprising an antenna device configured to be attached to said connector of said BTE prosthetic device, said antenna device comprising:
    a second connector configured to be attached to said connector of said BTE prosthetic device;
    an impedance matching circuit; and
    a lead configured to be attached to said second connector, wherein the impedance matching circuit adapts the impedance of said lead to the impedance of said transceiver of said BTE prosthetic device, and wherein said lead is operable as an extension of said electromagnetic antenna.

26. A behind-the-ear (BTE) prosthetic device for use in a medical system comprising:
    means for mechanically attaching an ear hook to said BTE prosthetic device; and
    means for one or more of transmitting and receiving an RF signal;
    wherein said means for attaching said ear hook to said BTE prosthetic device is configured to provide a means for wireless communication between said BTE prosthetic device and one or more other components of said system;
    wherein said means for mechanically attaching said ear hook to said BTE prosthetic device comprises an electrically conductive outer body configured to be connected to said means for one or more of transmitting and receiving an RF signal.

27. The BTE prosthetic device of claim 26, wherein said means for wireless communication between said BTE prosthetic device and one or more other components of said system comprises an electromagnetic antenna.

* * * * *